(12) United States Patent
Kanao et al.

(10) Patent No.: US 8,449,742 B2
(45) Date of Patent: May 28, 2013

(54) GAS SENSOR AND METHOD OF MANUFACTURING SAME

(75) Inventors: Keiji Kanao, Aichi-ken (JP); Kaneo Buma, Oobu (JP); Masato Ozawa, Toyota (JP); Hirofumi Noda, Kariya (JP); Kouichi Hirano, Okazaki (JP)

(73) Assignee: Denso Corporation, Kariya (JP)

( * ) Notice: Subject to any disclaimer, the term of this patent is extended or adjusted under 35 U.S.C. 154(b) by 287 days.

(21) Appl. No.: 12/765,985

(22) Filed: Apr. 23, 2010

(65) Prior Publication Data

US 2010/0269568 A1 Oct. 28, 2010

(30) Foreign Application Priority Data

Apr. 23, 2009 (JP) ................................. 2009-104659

(51) Int. Cl.
*G01N 27/407* (2006.01)
(52) U.S. Cl.
USPC ............................ 204/426; 204/424; 205/781
(58) Field of Classification Search
USPC ................. 204/410, 424, 426, 428, 429, 431, 204/432; 205/781, 783.5–785, 787; 73/23.31, 73/23.32
See application file for complete search history.

(56) References Cited

U.S. PATENT DOCUMENTS

| 5,246,562 A | 9/1993 | Weyl et al. |
| 2009/0101503 A1* | 4/2009 | Kanao ........................... 204/424 |

FOREIGN PATENT DOCUMENTS

| EP | 0 506 897 | 12/1995 |
| WO | WO 92/08127 | 5/1992 |

* cited by examiner

*Primary Examiner* — Keith Hendricks
*Assistant Examiner* — Susan D Leong
(74) *Attorney, Agent, or Firm* — Nixon & Vanderhye P.C.

(57) ABSTRACT

The gas sensor includes a sensor element having electrode pads formed in its electrode forming surfaces at the proximal end portion thereof, an insert-holding insulator insert-holding the sensor element, a housing insert-holding the insert-holding insulator, and a terminal unit. The proximal end portion of the sensor element is held by the terminal unit which includes a pair of proximal end insulators formed with metal terminals at their inner surfaces, and a spring member pressing the proximal end insulators in a direction that they approach each other. Each of the proximal end insulators includes an insulator contact portion in contact with one of the electrode forming surfaces. The insulator contact portion is located closer to the proximal end of the sensor element than a terminal contact portion at which the metal terminal contacts a corresponding one of the electrode pads.

10 Claims, 24 Drawing Sheets

GAS SENSOR AND METHOD OF MANUFACTURING SAME

CROSS-REFERENCE TO RELATED APPLICATION

This application is related to Japanese Patent Application No. 2009-104659 filed on Apr. 23, 2009, the contents of which are hereby incorporated by reference.

BACKGROUND OF THE INVENTION

1. Field of the Invention

The present invention relates to a gas sensor for detecting a concentration of a specific gas contained in a gas under measurement, and a method of manufacturing the gas sensor.

2. Description of Related Art

There is known a gas sensor for detecting a concentration of a specific gas contained in a gas under measurement, the gas sensor including a sensor element having a structure in which a sensor cell made of an oxygen ion-conductive solid electrolyte body provided with sensor electrodes at its both surfaces, and a heater including a heat generating section to generate heat for heating the sensor cell are formed integrally with each other. For example, refer to EP Patent Application Publication No. 0506897. This sensor element includes two pairs of electrode pads respectively connected to the heat generating section and the sensor electrodes. These electrode pads of the two pairs are formed at a surface of a portion of the sensor element which is closer to the proximal end of the sensor element than a portion at which the sensor element is insert-held by an insert-holding insulator. These electrode pads are formed such that two of them are arranged side by side on one of the two electrode forming surfaces parallel to each other of the sensor element, and the other two of them are arranged side by side on the other of the two electrode forming surfaces of the sensor element.

In more detail, as shown in FIG. 31, metal terminals 932 respectively connected to external leads are disposed in contact with their respective metal electrode pads 921. The metal terminals 932 are four in number and disposed such that two of them are arranged on the inner surface of one of proximal end insulators 931 of one pair disposed to hold a proximal end portion 922 of the sensor element 92 at electrode forming surfaces 923 of the proximal end portion 922, and the other two of them are arranged on the inner surface of the other of the proximal end insulators 931. The proximal end insulators 931 are pressed in the direction approaching each other by a spring member 933 of a ring shape disposed surrounding the proximal end side insulators 931. This keeps the two pairs of the metal terminals 932 in a state of being abutted against the two pairs of the electrode pads 921, respectively.

However, since the above gas sensor uses the proximal end insulators separated from each other, it has a problem in that the metal terminals 932 tends to move relative to the electrode forming surfaces of the sensor element when the metal terminals are connected to their leads, or when a bush is installed in the vicinity of the proximal end portion of the gas sensor during assembly of the gas sensor. The contact pressure of the metal terminal to the electrode pad may be reduced significantly especially when the metal terminal is applied with a force which causes the metal terminal to move away from the sensor element.

The variation in the contact pressure between the metal terminal and the electrode pad causes variation in the contact electrical resistance therebetween, as a result of which the detection accuracy of the sensor cell may be lowered, and the activation time of the sensor cell may be prolonged.

SUMMARY OF THE INVENTION

The present invention provides a gas sensor comprising:

a sensor element including a sensor cell and a heater integrally formed each other, the sensor cell being made of an oxygen ion-conductive solid electrolyte body provided with sensor electrodes at both surfaces thereof, the heater including a heat generating section to generate heat for heating the sensor cell;

an insert-holding insulator insert-holding the sensor cell; and a housing insert-holding the insert-holding insulator;

the sensor element including first and second pairs of electrode pads formed at portions thereof which are closer to a proximal thereof in an longitudinal direction of the gas sensor than a portion thereof at which the sensor element is insert-held by the insert-holding insulator, the electrode pads of the first pair being electrically connected to the heating section, the electrode pads of the second pair being connected to the sensor electrodes, the electrode pads of the first pair being arranged side by side on a first electrode forming surface of the sensor element, the electrode pads of the second pair being ads are arranged side by side on a second electrode forming surfaces of the sensor element, the first and second electrode forming surfaces being parallel to each other, the gas sensor further comprising a terminal unit including a pair of proximal end insulators holding therebetween a proximal end portion of the sensor element at the first and second electrode forming surfaces, first and second pairs of metal terminals respectively provided in inner surfaces of the pair of the proximal end insulators, and a spring member pressing the pair of the proximal end insulators in a direction that the proximal end insulators approach each other, each of the metal terminals of the first pair being connected to corresponding one of the electrodes pads of the first pair at a terminal contact portion thereof, each of the metal terminals of the second pair being connected to corresponding one of the electrodes pads of the second pair at a terminal contact portion thereof, each of the pair of the proximal end insulators including an insulator contact portion in contact with a corresponding one of the first and second electrode forming surfaces, the insulator contact portion of each of the pair of the proximal end insulators being located closer to the proximal end the sensor element than the terminal contact portion of a corresponding one of the first and second pairs of the metal terminals.

The present invention also provides a method of manufacturing a gas sensor, the gas sensor including:

a sensor cell and a heater integrally formed each other, the sensor cell being made of an oxygen ion-conductive solid electrolyte body provided with sensor electrodes at both surfaces thereof, the heater including a heat generating section to generate heat for heating the sensor cell;

an insert-holding insulator insert-holding the sensor cell; and a housing insert-holding the insert-holding insulator;

the sensor element including first and second pairs of electrode pads formed at portions thereof which are closer to a proximal end thereof in an longitudinal direction of the gas sensor than a portion thereof at which the sensor element is insert-held by the insert-holding insulator, the electrode pads of the first pair being electrically connected to the heating section, the electrode pads of the second pair being connected to the sensor electrodes, the electrode pads of the first pair being arranged side by side on a first electrode forming surface of the sensor element, the electrode pads of the second pair being arranged side by side on a second electrode forming surface of the sensor element, the first and second electrode forming surfaces being parallel to each other, the method comprising the steps of:

fabricating a terminal unit including:

a pair of proximal end insulators holding therebetween a proximal end portion of the sensor element at the first and second electrode forming surfaces;

first and second pairs of metal terminals respectively provided in inner surfaces of the pair of the proximal end insulators; and a spring member pressing the proximal end insulators in a direction that the pair of the proximal end insulators approach each other;

each of the metal terminal of the first pair being connected to a corresponding one of the electrode pads of the first pair at a terminal contact portion thereof, each of the metal terminal of the second pair being connected to a corresponding one of the electrode pads of the second pair at a terminal contact portion thereof, each of the pair of the proximal end insulators including an insulator contact portion in contact with a corresponding one of the first and second electrode forming surfaces, separating the pair of the proximal end insulators by applying a separating force to the pair of the proximal end insulators against a pressing force of the spring member until a gap thicker than a distance between the first and second electrode forming surfaces is formed between the first and second pairs of the metal terminals;

inserting the proximal end portion of the sensor element between the metal terminals of the first and second pairs;

causing the first and second pairs of the metal terminals to contact the first and second pairs of the electrode pads respectively by removing the separating force, so that the proximal end portion of the sensor element is held by the terminal unit in a state of the proximal end insulators being respectively in contact with the first and second electrode forming surfaces; and locating the insulator contact portions at which the proximal end insulators respectively contact the first and second electrode forming surfaces closer to the proximal end of the sensor element than the terminal contact portions.

According to the present invention, there is provided a gas sensor which exhibits good and stable electrical conduction between electrode pads of a sensor element and metal terminals of a terminal unit, and method of manufacturing the gas sensor.

Other advantages and features of the invention will become apparent from the following description including the drawings and claims.

PREFERRED EMBODIMENTS OF THE INVENTION

First Embodiment

Figure 4:
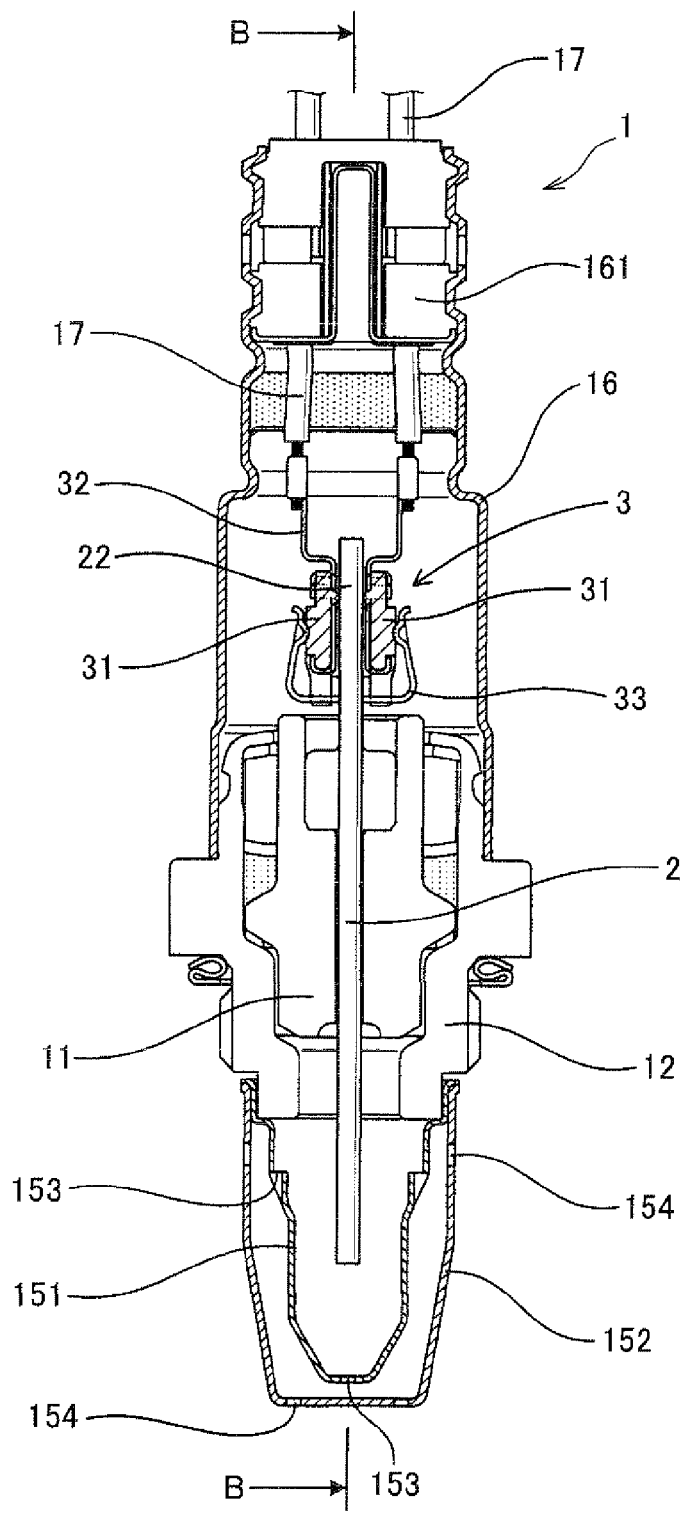
FIG. 4 is a cross-sectional view of the gas sensor according to the first embodiment of the invention.
Figure 5:
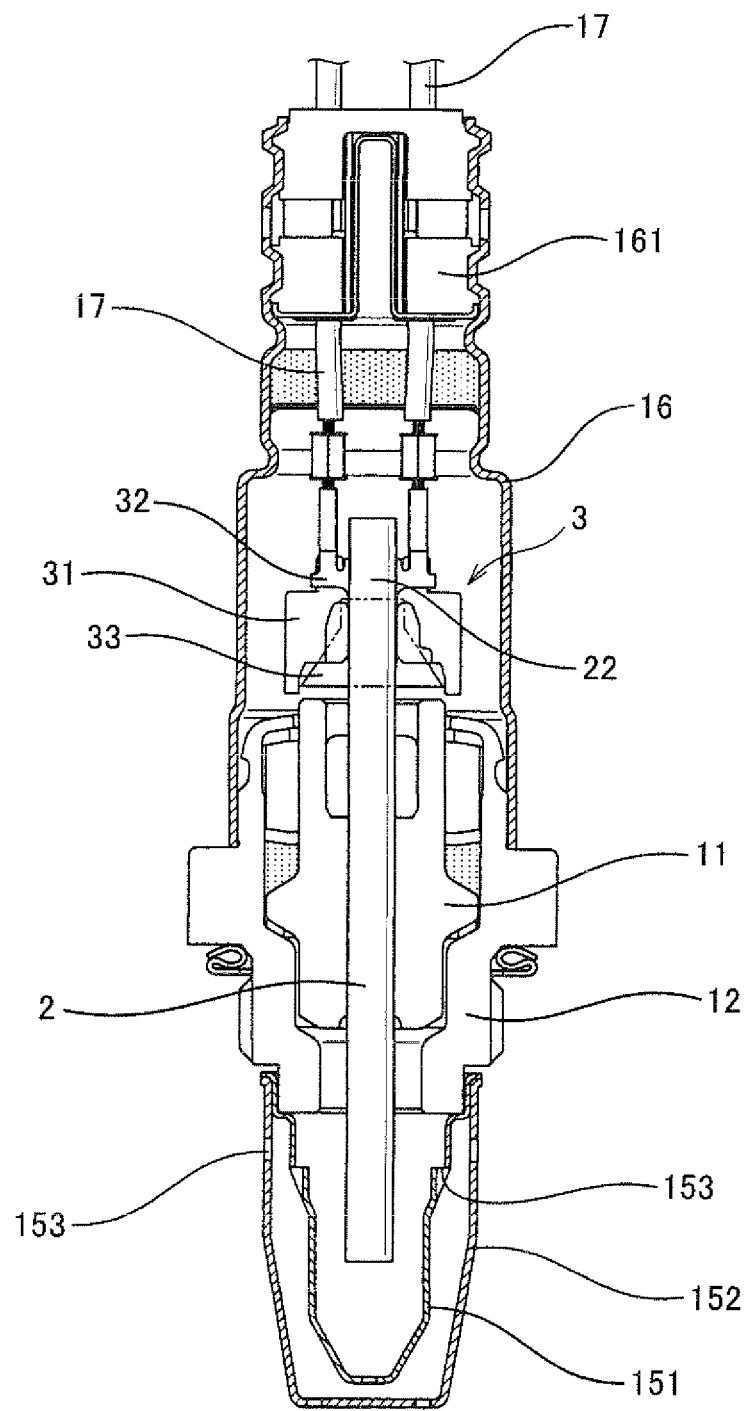
FIG. 5 is a cross-sectional view of FIG. 4 taken along the line B-B.

As shown in FIGS. 4 and 5, a gas sensor 1 according to a first embodiment of the invention includes a sensor element 2, an insert-holding insulator 11, and a housing 12. The sensor element 2 has a structure in which a sensor cell made of an oxygen ion-conductive solid electrolyte body provided with sensor electrodes at its both surfaces, and a heater including a heat generating section to generate heat for heating the sensor cell are formed integrally with each other. The insert-holding insulator 11 insert-holds the sensor element 2. The housing 12 insert-holds the insert-holding insulator 11.

Figure 3:
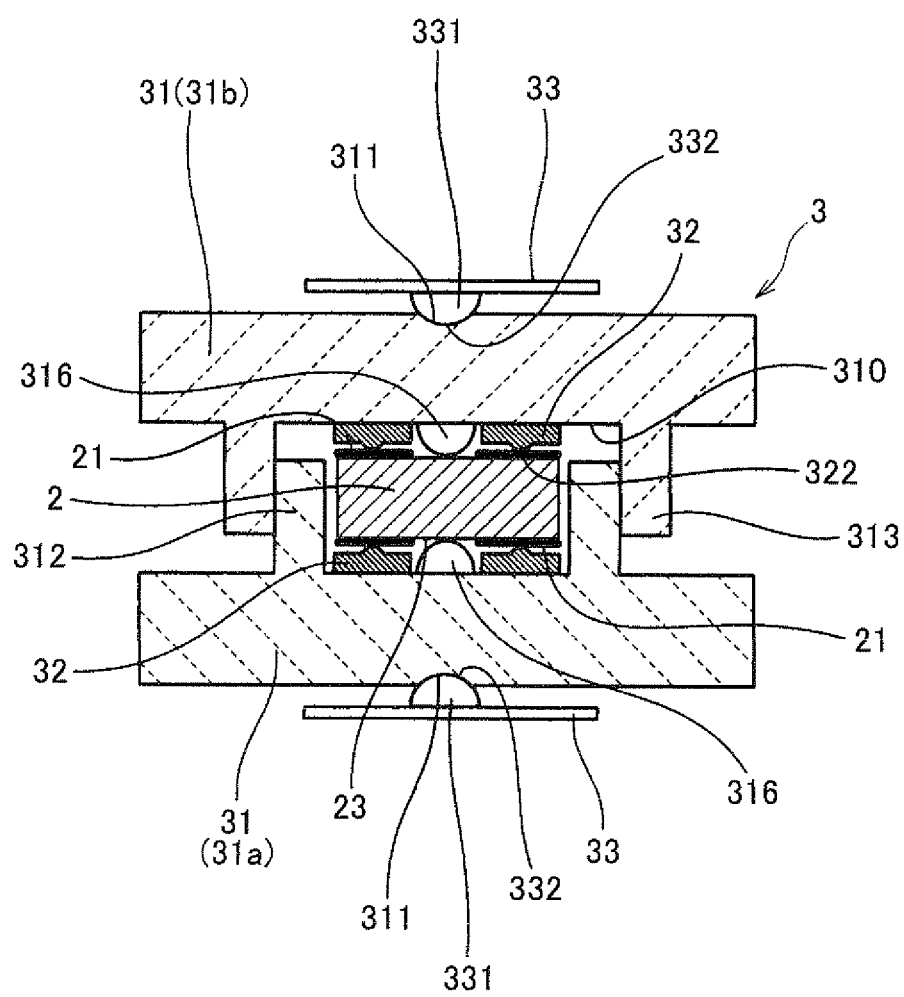
FIG. 3 is a cross-sectional view of FIG. 1 taken along the line A-A.
Figure 6:
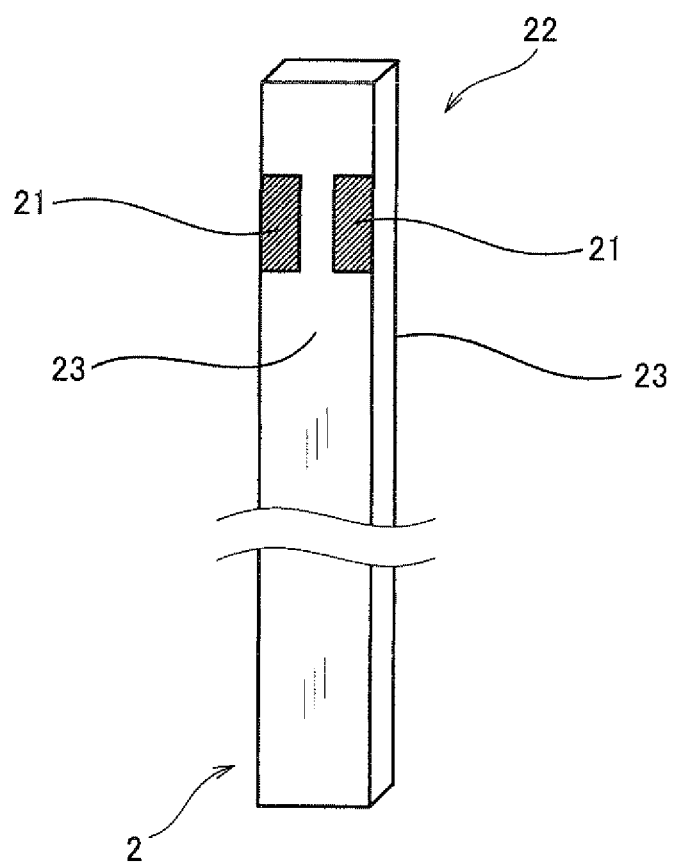
FIG. 6 is a perspective view of the sensor element included in the gas sensor of the first embodiment.

As shown in FIGS. 3 and 6, the sensor element 2 includes two pairs of electrode pads 21 respectively electrically connected to the heating generating section and the sensor electrodes. These electro pads 21 are formed at a proximal end portion 22 of the sensor element 2 which is closer to the proximal end of the sensor element 2 than a portion of the sensor element 2 which is insert-held by the insert-holding holding insulator 11. The electrode pads 21 are formed such that two of them are arranged side by side on one of two electrode forming surfaces 23 parallel to each other of the sensor element 2, and the other two of them are arranged side by side on the other of the two electrode forming surfaces 23.

Figure 1:
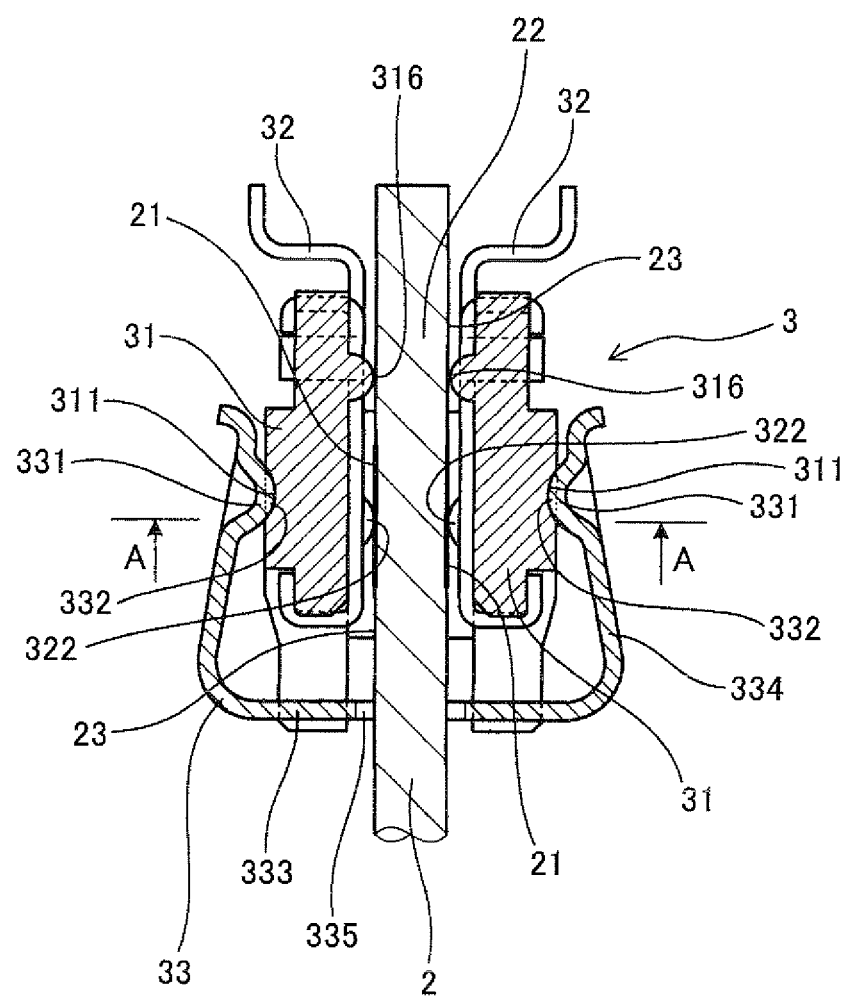
FIG. 1 is a cross-sectional view of a terminal unit holding a sensor element included in a gas sensor according to a first embodiment of the invention.

As shown in FIGS. 1, 3 and 4, the proximal end portion 22 of the sensor element 22 is held by a terminal unit 3. The terminal unit 3 includes a pair of proximal end insulators 31, metal terminals 32 and a spring member 33. The metal terminals 32 are provided in the inner surfaces of the respective proximal end insulators 31 so as to be in contact with corresponding respective ones of the electrode pads 21. The spring member 33 presses the proximal end insulators of the pair in the direction that they approach each other.

Figure 2:
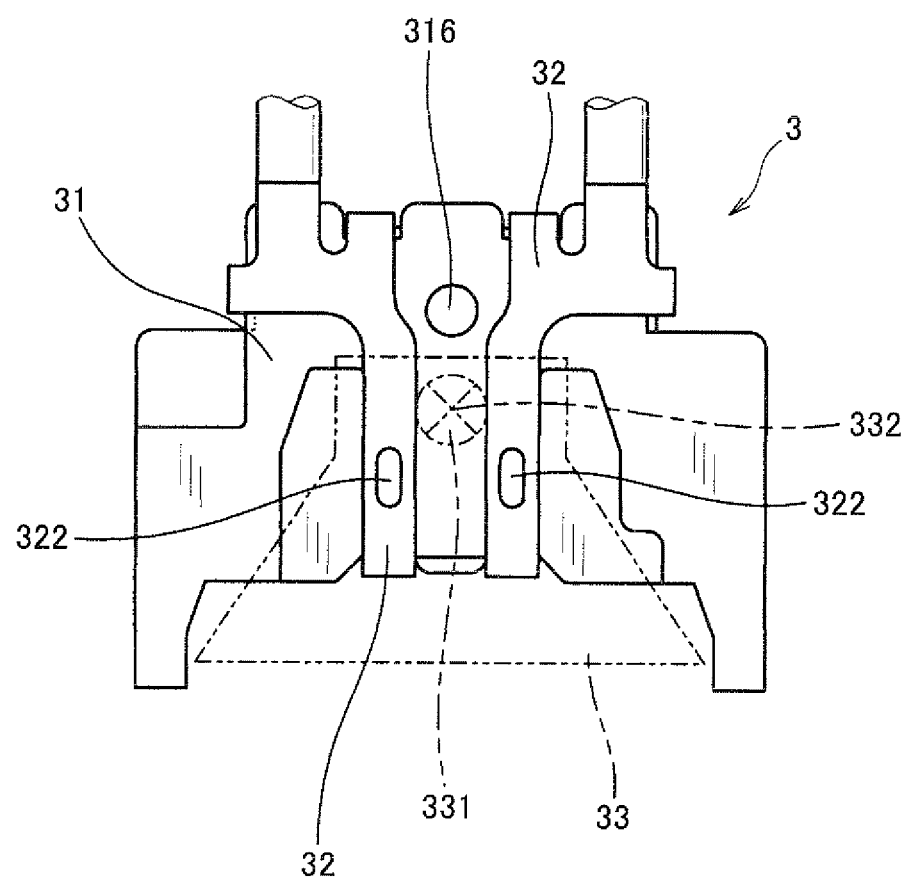
FIG. 2 is an explanatory view showing a positional relationship among proximal end insulators, metal terminals and a spring member in the gas sensor of the first embodiment.

As shown in FIGS. 1 and 2, each of the proximal end insulators 31 includes an insulator contact portion 316 which is in contact with one of the electrode forming surfaces 23 of the sensor element 2. The insulator contact portion 316 is closer to the proximal end of the sensor element 2 than terminal contact portion 322 provided in the metal terminals 32, each of the terminal contact portions 322 being in contact with a corresponding one of the electrode pads 21. Each of the insulator contact portions 316 projects in a semispherical shape toward the sensor element 2 from the surface of the proximal end insulators 31.

The spring member 33 includes convex portions 331. The proximal end insulator 31 includes a concave portion 311 to receive therein one of the convex portions 331 of the spring member 33. As shown in FIG. 2, the spring member 33 presses the proximal end insulators 31 at a respective single pushing point 332. The pushing point 332 is at such a position that it is projected within the triangle T shown in FIG. 7 formed by connecting by straight lines the insulator contact point 316 and the terminal contact portions 322 of the pair on one of the electrode forming surfaces on the side of this pushing point 332.

Figure 8:
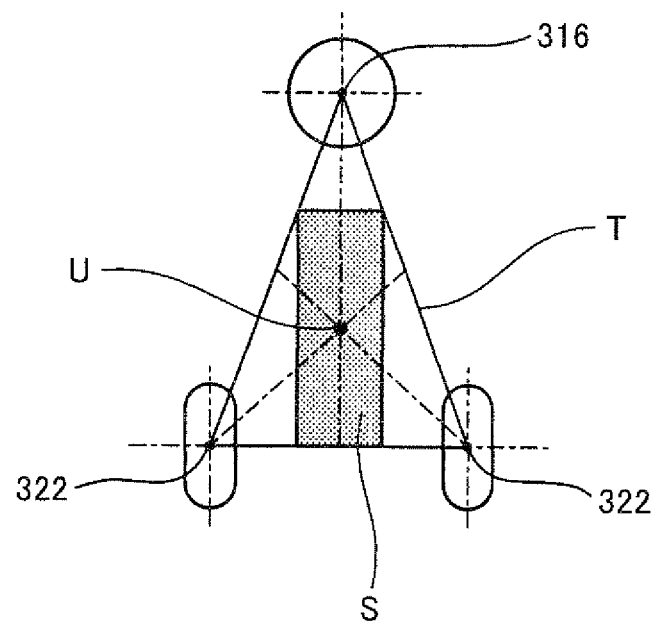
FIG. 8 is an explanatory view showing another positional relationship among the terminal contact portions, insulator contact portion and pressing point in the gas sensor of the first embodiment.

It is preferable that the pushing point 332 is at such a position that it is projected within the rectangle S shown in FIG. 8 which share the same median point U with the triangle T. The width of this rectangle S in the cross-longitudinal direction is half the distance between the terminal contact portions 322 of the pair, and the length of this rectangle S in the longitudinal direction is ⅔ of the height of the triangle T. It is still more preferable that the pushing point 332 is at such a position that it is projected to a substantially median point U of the triangle T, so that the pushing point 322 is projected within an area whose center is at the median point U and which extends 0.2 mm in the longitudinal and cross-longitudinal directions, in view of variation in size of the parts of the gas sensor and assembly variation.

As shown in FIG. 2, the convex portion 331 of the spring member 31 has a plan view of a circle whose center serves as the pressing point 332. Each metal terminal 32 includes a convex portion projecting toward the sensor element 2 to serve as the terminal contact portion 322 at the median point in the plan view thereof. Also, each proximal end insulator 31 includes a convex portion projecting toward the sensor element 2 to serve as the insulator contact portion 316 at the median point in the plan view thereof.

Figure 16:
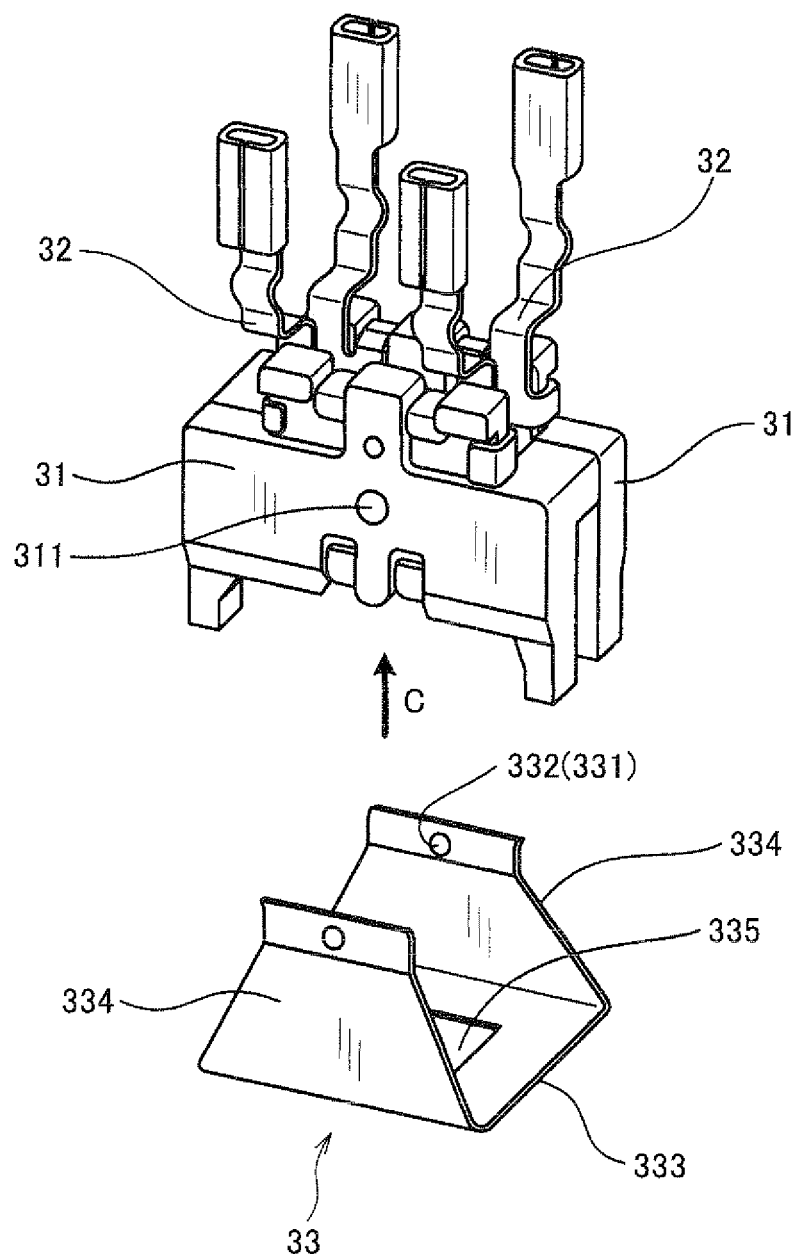
FIG. 16 is a perspective view of the proximal end insulators of the pair set with the metal terminals and combined with each other.

The spring member 33 is made of a leaf spring. As shown in FIGS. 1 and 16, the spring member 33 is constituted of a bottom plate portion 333 of a flat plate shape and a pair of rising portions 334 rising from both sides of the bottom plate portion 333 and bent toward the same surface of the bottom plate portion 333. The convex portion 331 is formed in the vicinity of the distal end of each of the rising portions 334. The bottom plate portion 333 is formed with an opening 335 through which the sensor element 2 is inserted.

Figure 11:
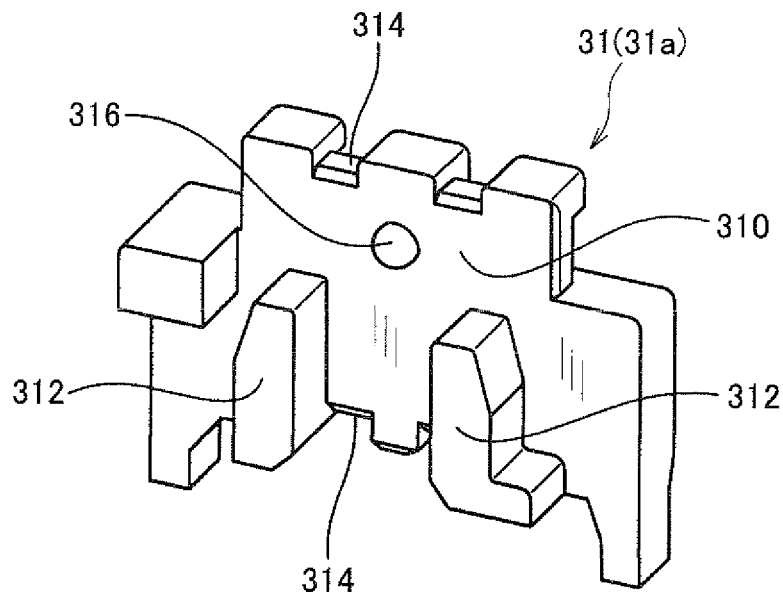
FIG. 11 is a perspective view of one of the proximal end insulators included in the gas sensor of the first embodiment.
Figure 12:
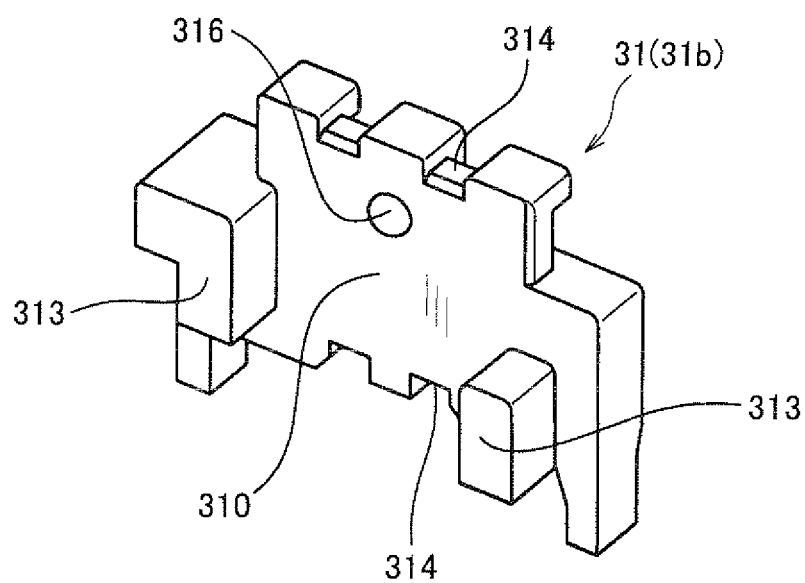
FIG. 12 is a perspective view of the other of the proximal end insulators included in the gas sensor of the first embodiment.
Figure 13:
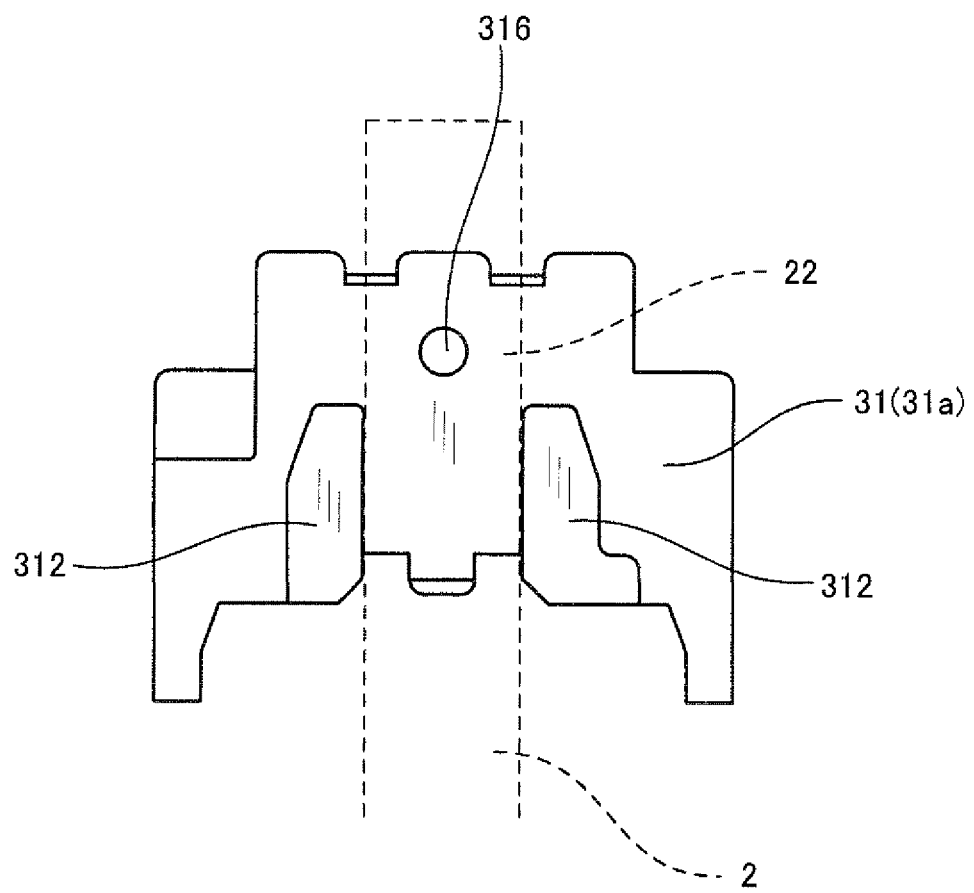
FIG. 13 is a front view of the one of the proximal end insulators set with the sensor element included in the gas sensor of the first embodiment.

As shown in FIGS. 3, 11 and 13, one of the proximal end insulators 31 (referred to as the "proximal end insulator 31a" hereinafter) includes a pair of sensor positioning projections 312 for positioning the sensor element 2 in the width direction of the sensor element 2 (the direction perpendicular to the longitudinal direction of the sensor element and parallel to the electrode forming surfaces). On the other hand, as shown in FIGS. 3 and 12, the other of the proximal end insulators 31 (referred to as the "proximal end insulator 31b" hereinafter) includes a pair of insulator positioning projections 313 for positioning itself with respect to the sensor positioning projections 312.

Figure 14:
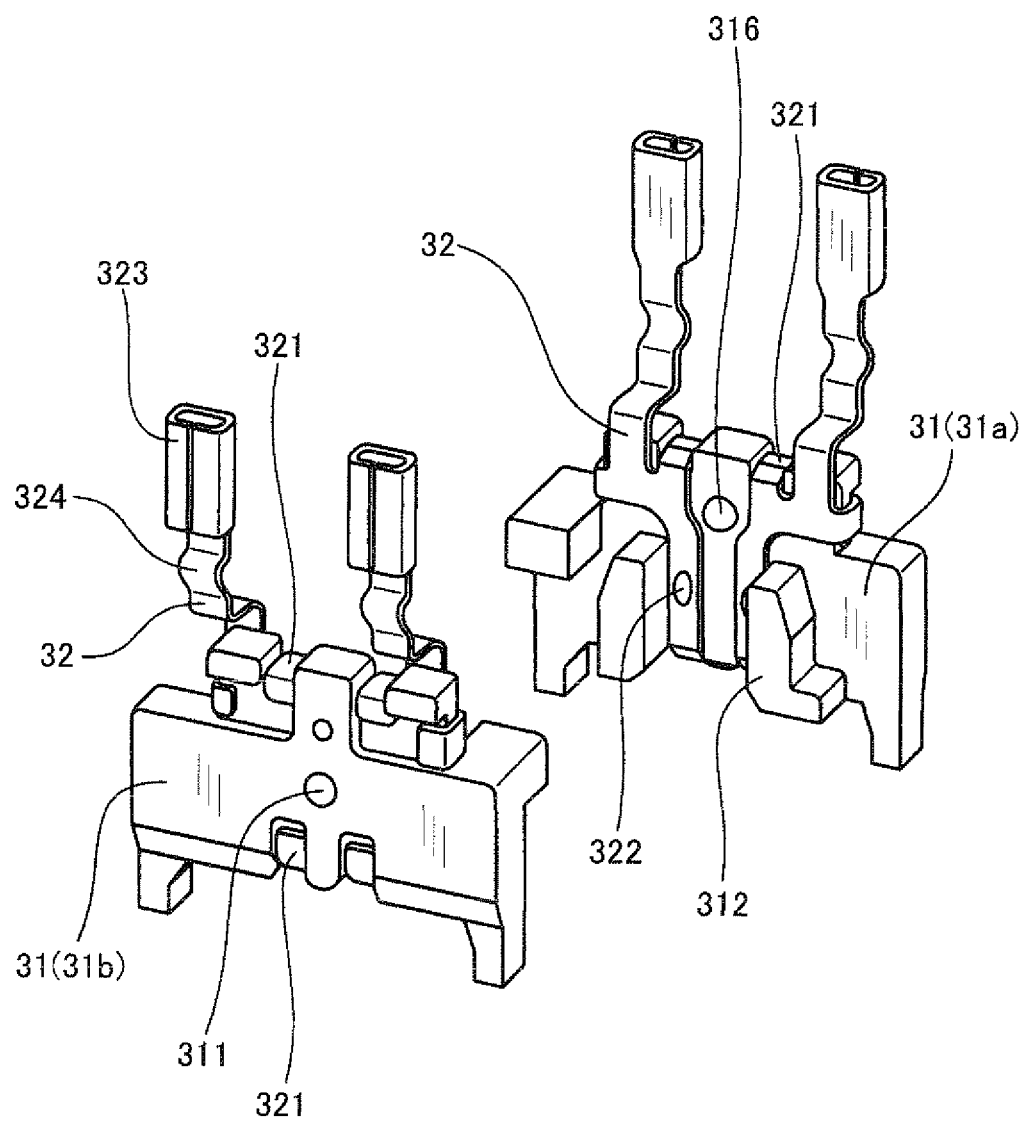
FIG. 14 is a perspective view of the proximal end insulators of the pair each installed with the metal terminals included in the gas sensor of the first embodiment.
Figure 15:
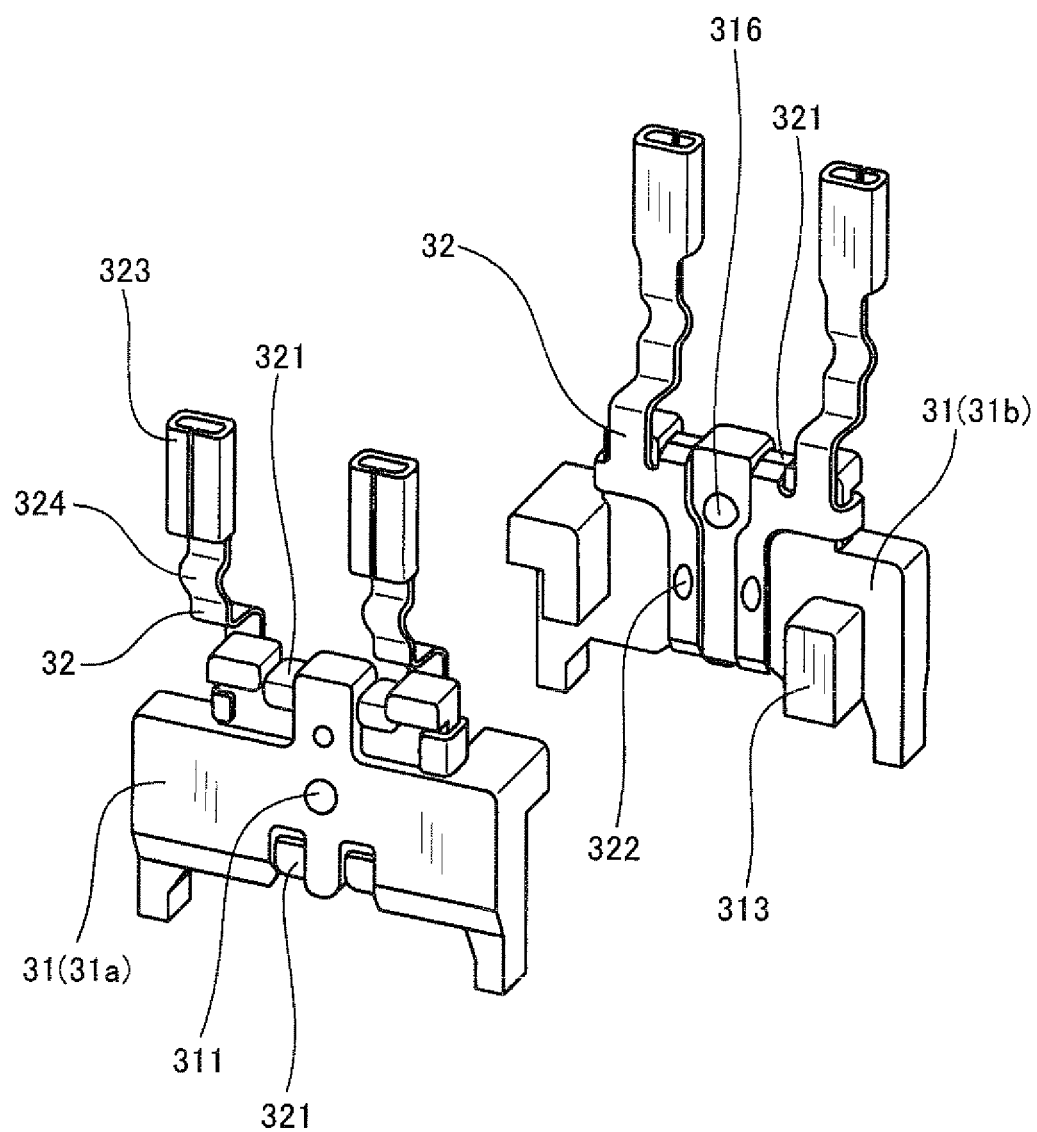
FIG. 15 is a perspective view of the proximal end insulators of the pair each installed with the metal terminals included in the gas sensor of the first embodiment as viewed from the opposite side to FIG. 14.
Figure 20:
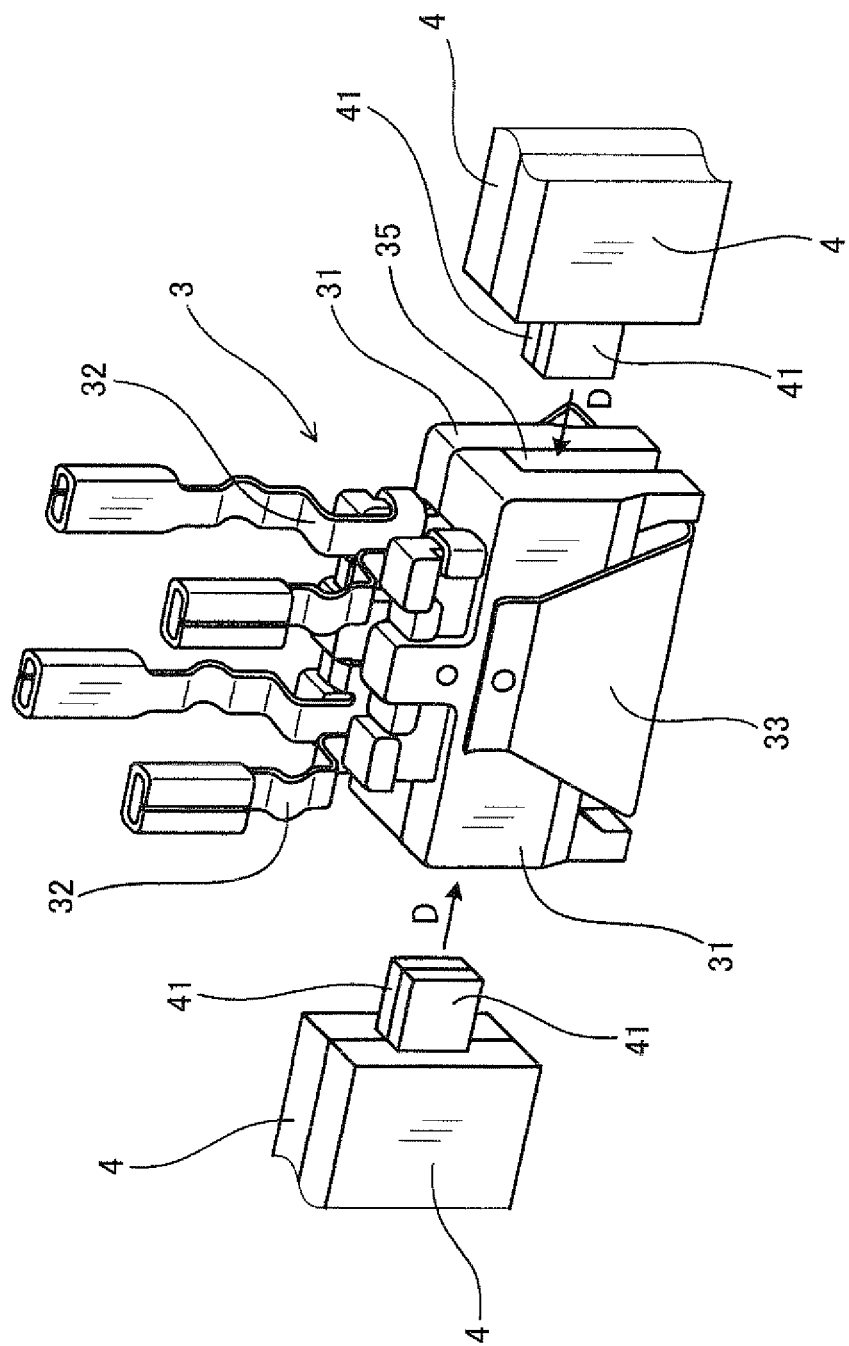
FIG. 20 is an explanatory perspective view showing the terminal unit included in the gas sensor of the first embodiment set with separating jigs at both sides thereof.

As shown in FIGS. 14 and 15, each of the proximal end insulators 31 includes the two metal terminals 32. Each metal terminal 32 is disposed in the inner surface 310 of either one of the proximal end insulators 31, which is not formed with the sensor positioning projections 312 or the insulator positioning projections 313. As shown in FIGS. 11 and 12, each of the proximal end insulators 31*a* and 31*b* is formed with two cutouts 314 at each of the proximal end portion and the distal end portion thereof. As shown in FIGS. 14 and 15, the metal terminals 32 are fitted into the cutouts 314 at their fitting portions 321. As shown in FIG. 20, the terminal unit 3 includes, between the proximal end insulators 31 of the pair, lateral concave portions 35 which extend in the direction perpendicular to the longitudinal direction of the sensor element 2 and in parallel to the electrode forming surfaces 23, and respectively open in the opposite directions.

As shown in FIGS. 4 and 5, the gas sensor 1 includes an inner element cover 151 and an outer element cover 152 at the distal end of the housing 12 to cover the distal end of the sensor element 2. The inner element cover 151 is formed with vent holes 153. The outer element cover 152 is formed with vent holes 154. The housing 12 is joined with a proximal end cover 16 to cover the terminal unit 3 at the proximal end thereof. The proximal end portion of the proximal end cover 16 is closed by a rubber bush 161. Leads 17 each electrically connected to a corresponding one of the metal terminals 32 penetrate through the rubber bush 161.

Figure 10:
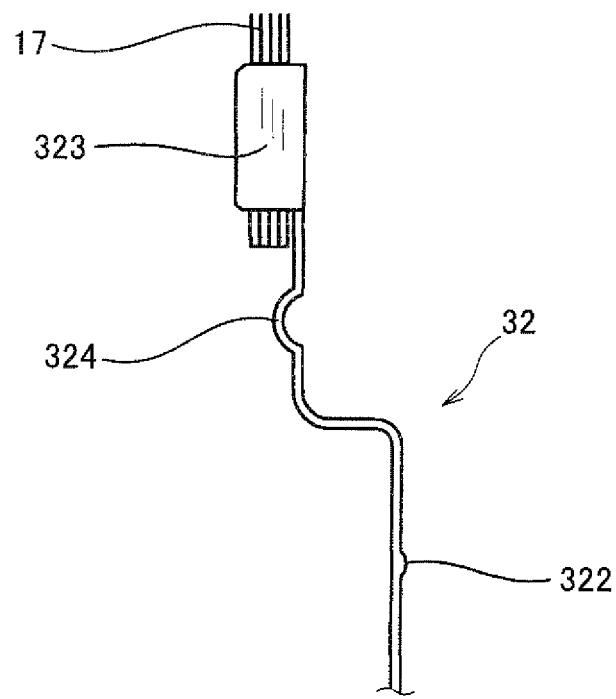
FIG. 10 is a side view of the metal terminal having a bent portion included in the gas sensor of the first embodiment.

The terminal unit 3 is not in contact with the proximal end cover 16 or the insert-holding insulator 11. As shown in FIG. 10, each metal terminal 32 includes a crimp-fixed portion 323 crimp-fixed to one end of the lead 17, and a bent portion 324 located between the crimp-fixed portion 323 and the terminal contact portion 322. As shown in FIGS. 1, 4 and 5, the sensor element 2 projects toward the proximal end side of the gas sensor beyond the proximal end of the terminal unit 3.

Next, a method of manufacturing the gas sensor 1 is described.

Figure 17:
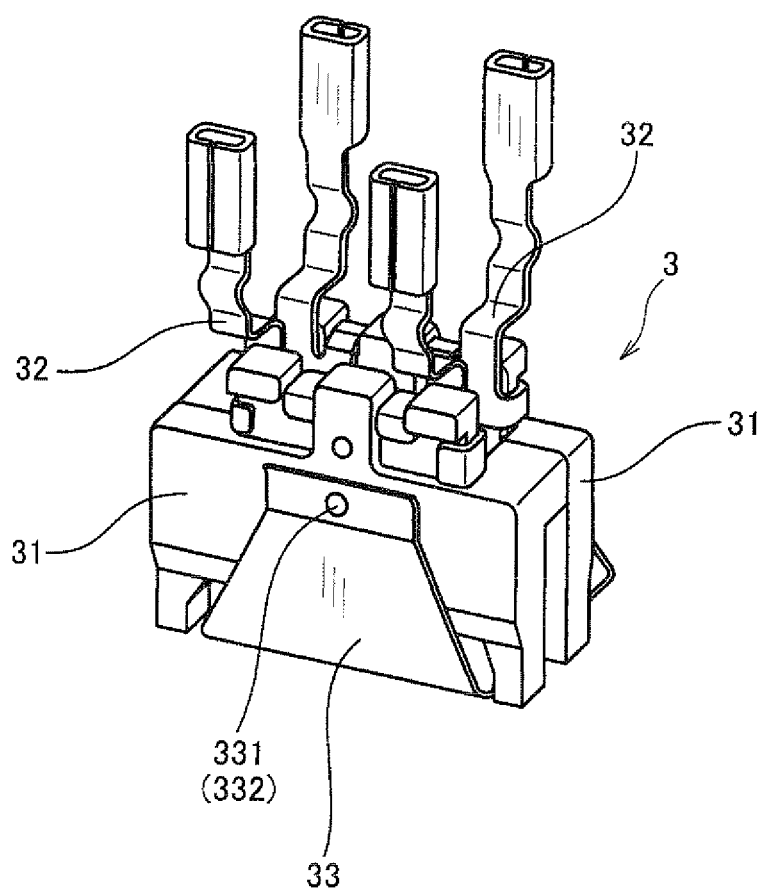
FIG. 17 is a perspective view of the terminal unit included in the gas sensor of the first embodiment.

First, the terminal unit 3 is assembled as shown in FIGS. 14 to 19. In more detail, as shown in FIGS. 14 and 15, the two metal terminals 32 are installed to each of the proximal end insulators 31 of the pair. Next, as shown in FIG. 16, the proximal end insulators 31 installed with the metal terminals 32 are fitted together such that their inner surfaces 310 are opposed to each other. Next, as shown in FIGS. 16 and 17, the spring member 33 is fitted to the proximal end insulators 31 fitted together in the direction from the distal end side (in the direction indicated by the arrow C shown in FIG. 16). At this time, the convex portions 331 of the spring member 33 abut against the concave portions 311 respectively formed in the back surfaces of the proximal end insulators 31 (FIG. 1). This completes the terminal unit 3.

Figure 18:
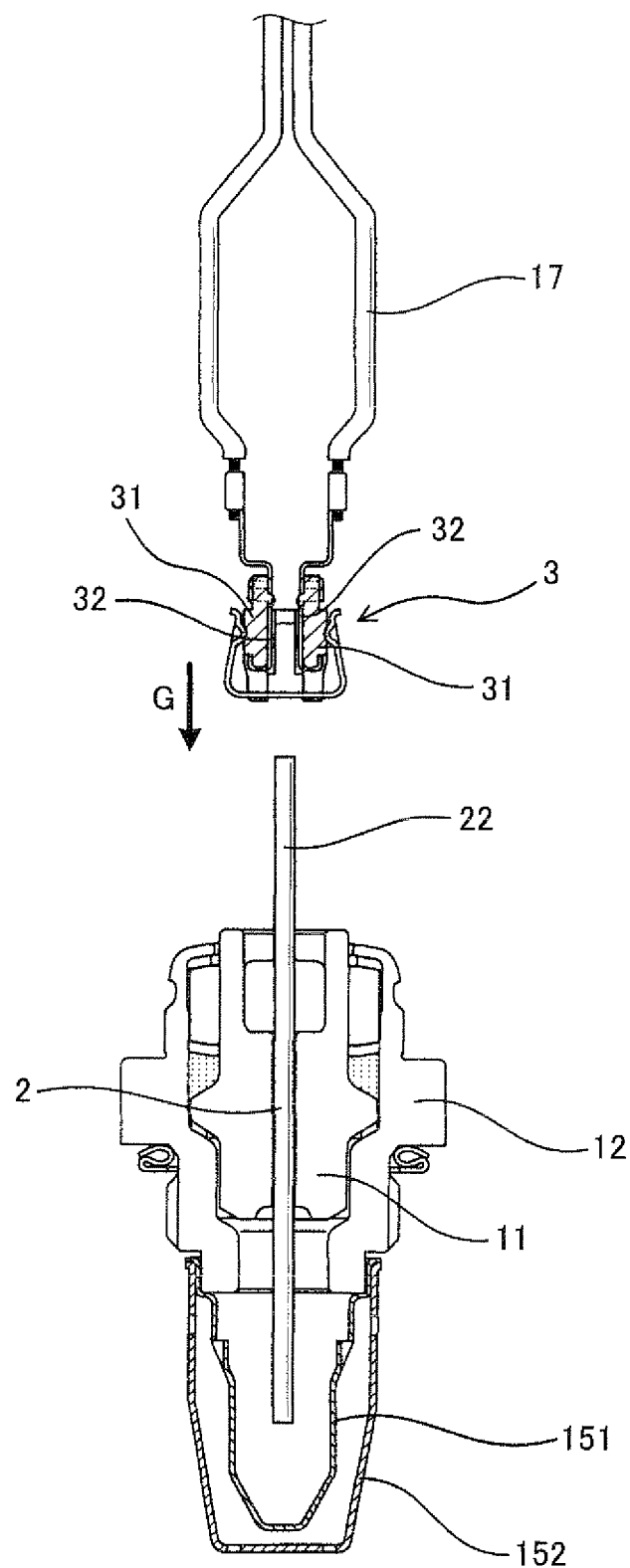
FIG. 18 is an explanatory view showing the sensor element and the terminal unit included in the gas sensor of the first embodiment before being assembled to each other.

As shown in FIG. 18, the sensor element 2 is prepared in a state of being inserted into the housing 12 and the insert-holding insulator 11. In this state where the sensor element 2 is inserted into and held by the insert-holding insulator 11 held by the housing 10, terminal unit 3 is installed on the proximal end portion 22 of the sensor element 2 as follows.

Figure 22:
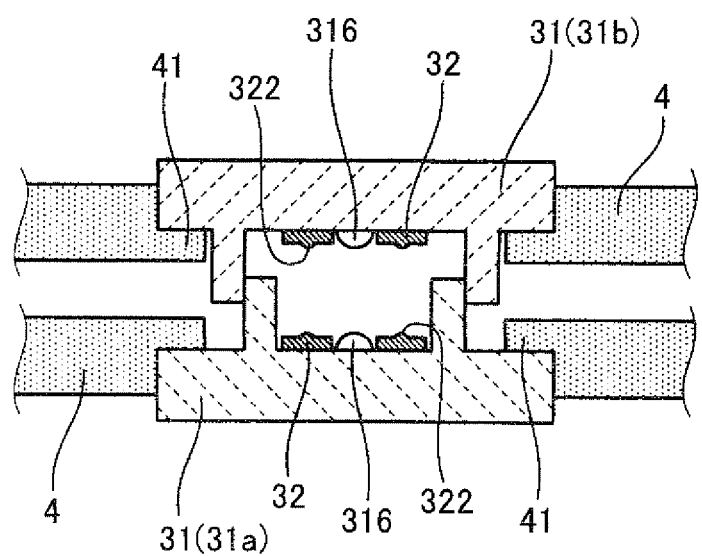
FIG. 22 is an explanatory cross-sectional view of the terminal unit included in the gas sensor of the first embodiment in a state of the distance between the metal terminals is extended by moving the separating jigs of the two pairs away from each other.

As shown in FIG. 22, the proximal end insulators 31 of the terminal unit 3 are applied with a separating force against the pressing force of the spring member 33, in order to separate the proximal end insulators 31 from each other until a gap thicker than the distance between the electrode forming surfaces 23 at the proximal end portion 22 of the sensor element 2 is formed between the two opposed pairs of the metal terminals 32.

Figure 21:
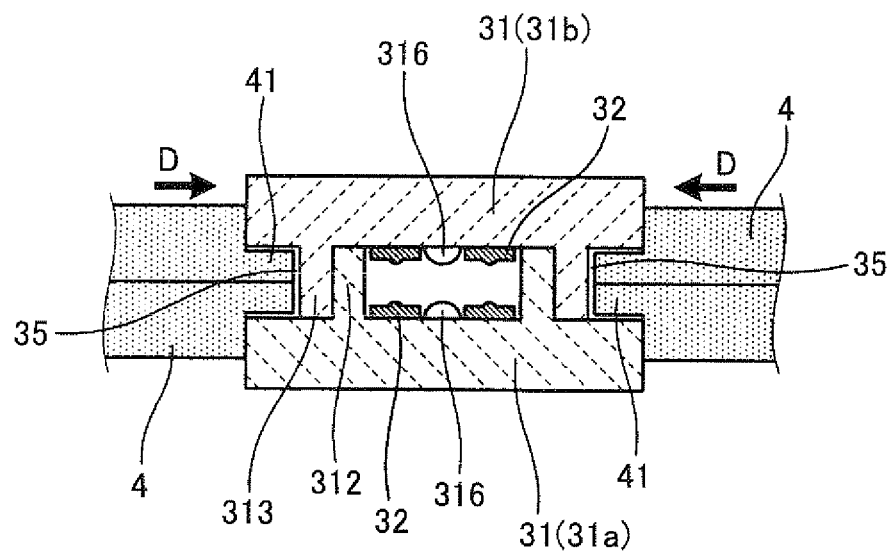
FIG. 21 is an explanatory cross-sectional view of the terminal unit included in the gas sensor of the first embodiment inserted with the separating jigs at lateral concave portions formed therein.

As a result, as shown in FIGS. 20 and 21, the terminal unit 3 is formed with the lateral concave portions 35 opening laterally at its lateral surfaces. These lateral concave portions 35 are located between the proximal end insulators 31 of the pair. Next, two pairs of separating jigs 4 each including an insertion end 41 are set ready.

As shown in FIG. 20, the pair of the separating jigs 4 are placed on the lateral sides of the terminal unit 3 in the state of their insertion ends 41 of each pair being put on each other. Subsequently, as shown in FIG. 21, two sets of the insertion ends 41 put on each other are respectively inserted into the lateral concave portions 35 of the terminal unit 3 in the directions indicated by the arrow D shown in FIGS. 20 and 21.

Next, as shown in FIG. 22, the insertion ends 41 of each of the separating jigs 4 are moved in the direction that they separate from each other. As a result, the proximal end insulators 31 of the pair latched by the insertion ends 41 move in the direction that they separate from each other. At this time, a gap thicker than the thickness of the proximal end portion 22 of the sensor element 2 is formed between the opposed meta terminals 32 installed on the proximal end insulators 31 of the pair.

Figure 19:
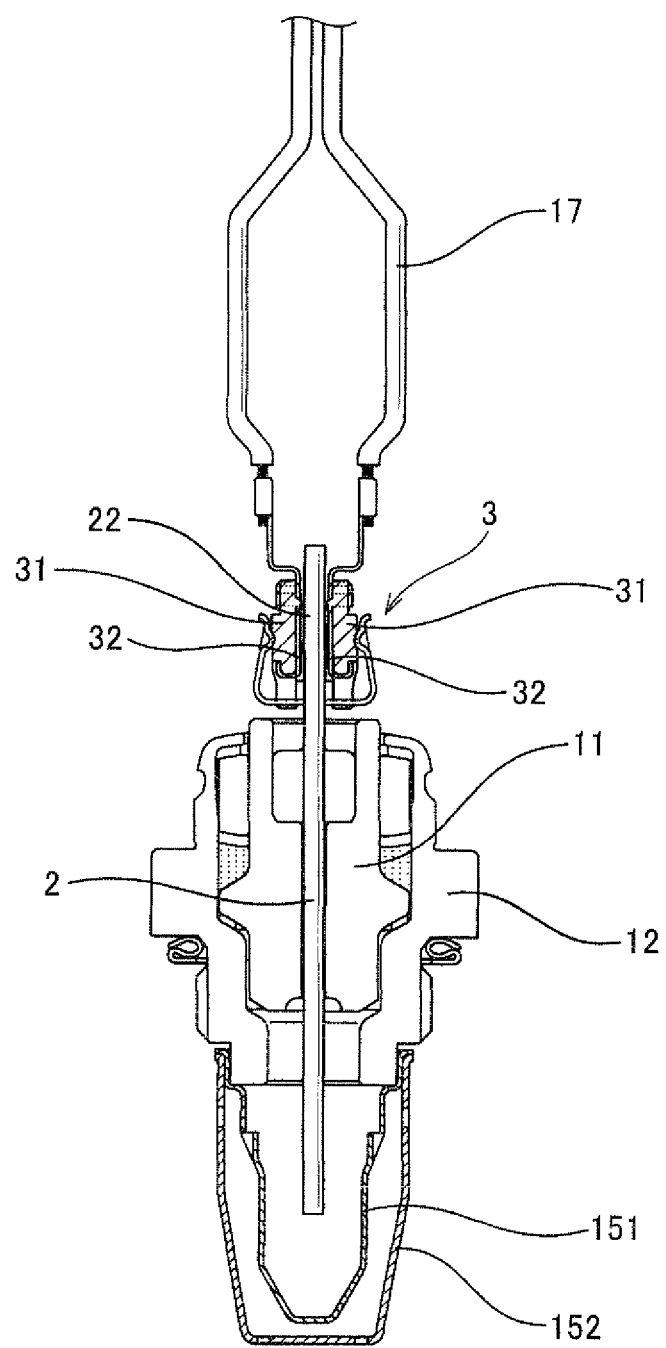
FIG. 19 is an explanatory view showing the sensor element and the terminal unit included in the gas sensor of the first embodiment after being assembled to each other.
Figure 23:
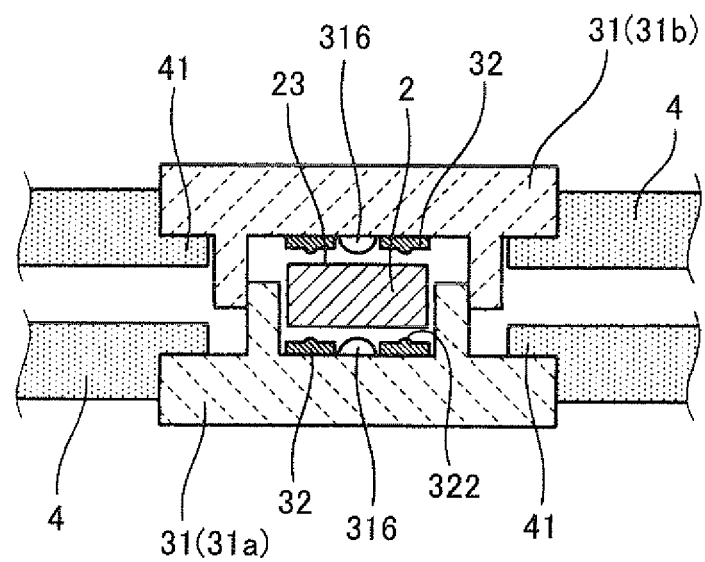
FIG. 23 is an explanatory cross-sectional view showing the metal terminals between which the proximal end portion of the sensor element is inserted in the gas sensor of the first embodiment.
Figure 24:
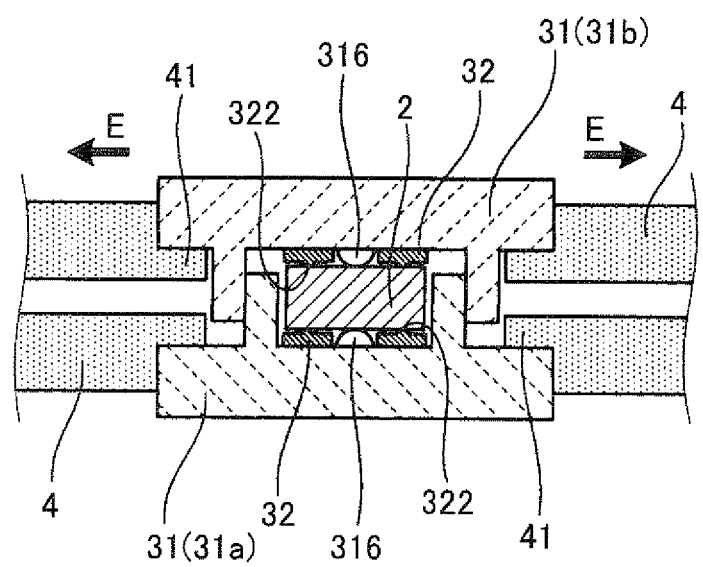
FIG. 24 is an explanatory cross-sectional view showing the terminal unit holding the proximal end portion of the sensor element in the gas sensor of the first embodiment.

Next, as shown in FIGS. 18, 19 and 23, the end portion 22 of the sensor element 2 is inserted between the opposed metal terminals 32 of the two pairs in the direction indicated by the arrow G shown in FIG. 18. Subsequently, as shown in FIG. 24, the separating force applied to the proximal end insulators 31 of the pair is removed, so that the proximal end portion 22 of the sensor element 2 is held by the terminal unit 3 in the state of the metal terminals 32 of the two pairs being in contact with their corresponding electrode pads 21 of the sensor element 2.

That is, by putting the separating jigs 4 of the two pairs on each other again, the sensor element 2 is held by the proximal end insulators 31 and the metal terminals 32 at the proximal end portion 22 thereof. At this time, the insulator contact portions 316 of the proximal end insulators 31 abut against the electrode forming surfaces 23 of the sensor element 2, and the terminal contact portions 322 of the metal terminals 32 installed on the proximal end insulators 31 abut against the electrode pads 21 of the sensor element 2.

Next, the separating jigs 4 are moved back in the directions that they distance from the terminal unit 3 (in the directions indicated by the arrow E shown in FIG. 24), and then the insertion ends 41 of the separating jigs 4 are pulled out from the lateral concave portions 35. As a result, the proximal end portion 22 of the sensor element 2 is held by the terminal unit 3. Thereafter, the proximal end cover 16 is joined to the proximal end portion of the housing 12 to cover the terminal unit 3 and other components to complete the gas sensor 1 as shown in FIGS. 4 and 5.

Next, the advantages provided by the first embodiment described above are explained. The proximal end insulator 31 has the insulator contact portion 316 in contact with the electrode forming surface of the sensor element 2. Accordingly, the proximal end insulator 31 to which the metal terminals 32 of the pair are fixed contacts the electrode forming surface 23 at three points. That is, in this embodiment, the proximal end insulator 31 to which the metal terminals 32 of the pair are fixed contacts the electrode forming surface 23 at the insulator contact portion 316 and the two terminal contact portions 322. This makes it possible to stabilize the state of the abutment between the proximal end insulator 31 to which the metal terminals 32 are fixed and the sensor element 2, that is, the holding state of the sensor element 2 by the terminal unit 3. Hence, according to this embodiment, it is possible to prevent the contact pressure between the electrode pads 21 and the metal terminals 32 to vary to thereby achieve stable electrical conduction therebetween.

Figure 25:
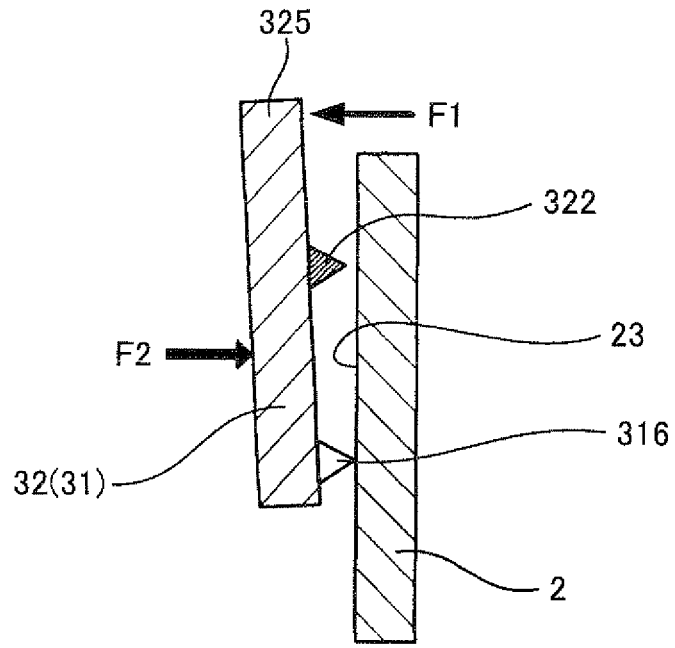
FIG. 25 is an explanatory view explaining a disadvantage when the terminal contact portions and the insulator contact portion are in a positional relationship opposite to that in the first embodiment.
Figure 26:
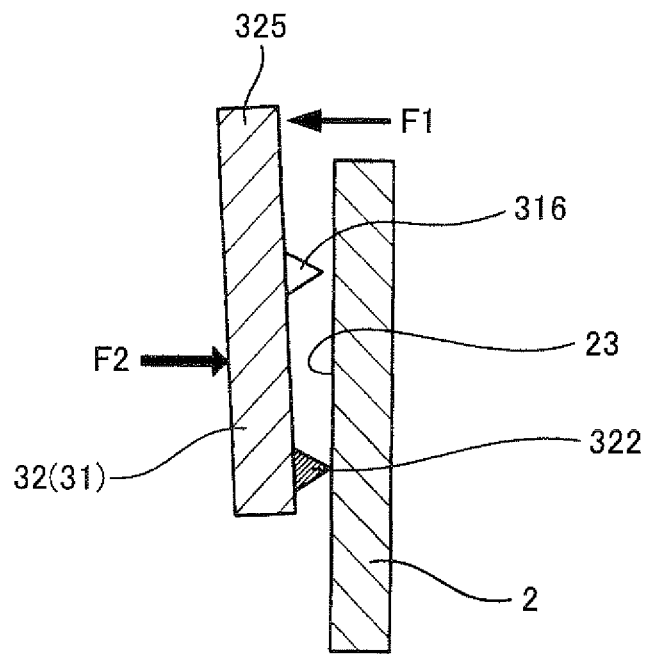
FIG. 26 is an explanatory view explaining effects depending on the positional relationship between the terminal contact portions and the insulator contact portion in the gas sensor of the first embodiment.

The insulator contact portion 316 is located closer to the proximal end side of the gas sensor in the longitudinal direction than the terminal contact portions 322. Accordingly, even when the metal terminals 32 are applied with an external force during assembly of the gas sensor 1, electrical conduction at the terminal contact portions can be maintained. This is explained in more detail as follows. During assembly of the gas sensor, as shown in FIGS. 25 and 26, an external force occurs at a proximal end portion 325 of the metal terminal 32 as a point of effort. Accordingly, in a case where the terminal contact portions 322 are located closer to the proximal end side than the insulator contact portion 316 as shown in FIG. 25, if a force F1 is applied to the proximal end portion 325 in a direction to move it away from the sensor element 2, the contact pressure of the terminal contact portion 322 may decrease causing poor electrical conduction, because the terminal contact portion 322 will lift from the electrode forming surface 23 with the insulator contact portion 316 serving as a fulcrum.

In this embodiment, as shown in FIG. 26, the terminal contact portions 322 are located closer to the longitudinally distal end side than the insulator contact portion 316, if such a force F1 is applied to the proximal end portion 325, the insulator contact portion 316 will lift from the electrode forming surface 23 (the electrode pad 21) with the terminal contact portions 322 serving as a fulcrum. However, it does not make a problem because the insulator contact portion 316 does not affect the detection accuracy of the sensor cell, and the contact pressure of the terminal contact portions 322 increases. Accordingly, good electrical conduction at the terminal contact portions 322 can be maintained.

When the force F is applied to the proximal end portion 325 of the metal terminal 32 in a direction to move it close to the sensor element 2, in the structure of this embodiment shown in FIG. 26, since the insulator contact portion 316 serves as a fulcrum, and the terminal contact portions 322 serve as a point of action, the terminal contact portions 322 are applied with a force in the direction to lift the terminal contact portions 322 from the electrode forming surface 23. However, to decrease the contact pressure of the terminal contact portions 322, a very large force is needed because the distance between the insulation contact portion 316 as a fulcrum and the point of effort in the proximal end portion 325 is small. Since the metal terminals 32 are not applied with a force large enough to decrease the contact pressure during assembly of the gas sensor, the detection accuracy of the sensor cell is not degraded. In FIGS. 25 and 26, F2 represents a pressing force of the spring member 33.

Since the insulator contact portion 316 projects toward the sensor element 2 from the proximal end insulator 31, it is possible to cause the insulator contact portion 316 to abut against the electrode forming surface 23 of the sensor element 2 easily and reliably. The insulator contact portion 316 is provided singly in each one of the proximal end insulators 31. Accordingly, since the terminal unit 3 abuts against the electrode forming surface 23 at three points including the insulator contact portion 316 and the two terminal contact portion, the sensor element 2 can be stably held by the terminal unit 3. This makes it possible to achieve stable electrical conduction at the terminal contact portions 322.

Figure 27:
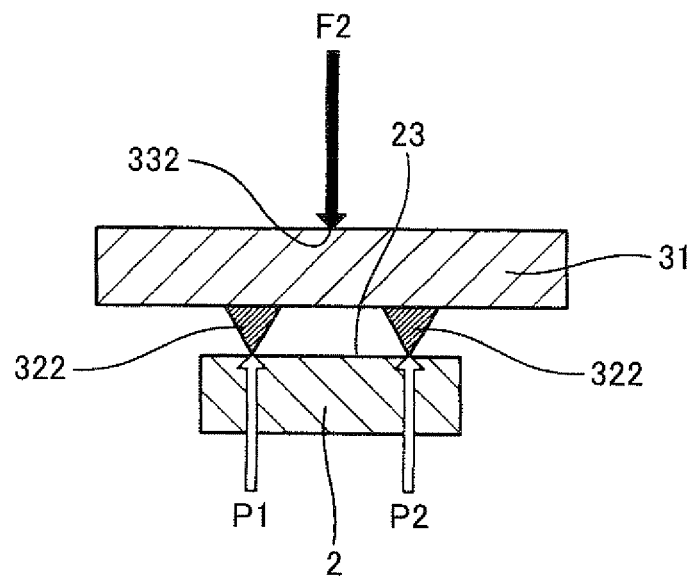
FIG. 27 is an explanatory view explaining an advantage when the pressing point is one in number in the gas sensor of the first embodiment.
Figure 28:
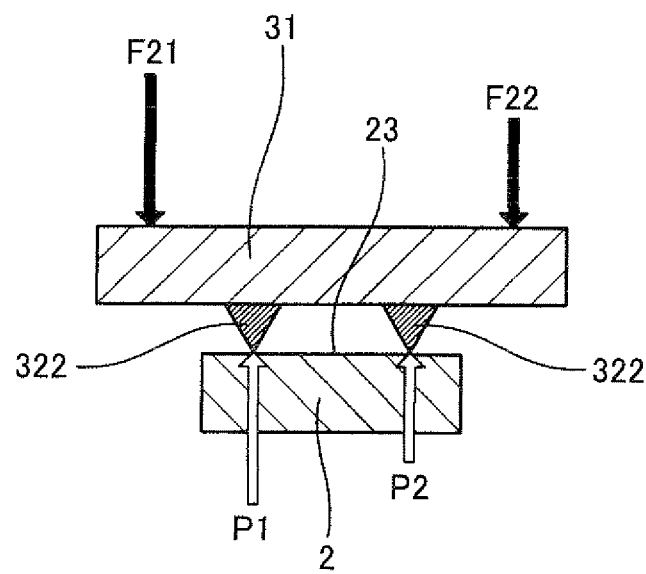
FIG. 28 is an explanatory view explaining a disadvantage when the pressing point is two in number.

The spring member 33 presses each of the proximal end insulators 31 at one pressing point 332. Accordingly, as shown in FIG. 27, the contact pressures P1 and P2 at the terminal contact portions 322 arranged in the width direction can be made equal to each other. In a case shown in FIG. 28 in which the spring member 33 presses each of the proximal end insulators 31 at two pressing points 332, if there occurs a difference between the pressing forces F21 and F22 at the pressing points 332, the contact pressures P1 and P2 may also differ from each other. In the case of this embodiment shown in FIG. 27 in which the spring member 33 presses each of the proximal end insulators 31 at one point, the pressing force F2 at this one point is equally distributed to the terminal contact portions 322 of the pair.

As shown in FIG. 1, the spring member 33 includes the convex portion 331, and the proximal end insulator 31 is formed with the concave portion 311 to receive therein the convex portion 331. Accordingly, since the spring member 33 and the proximal end insulator 31 can be accurately positioned with respect to each other, it is possible to reduce variation in the contact pressures at the terminal contact portions 322 and the insulator contact portion 316.

Figure 7:
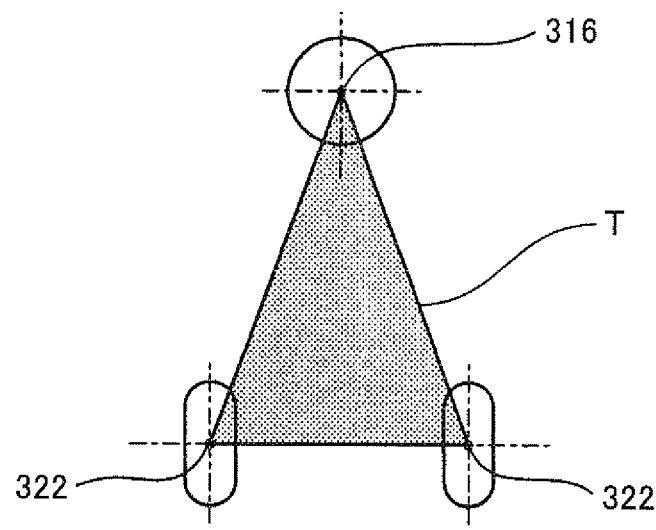
FIG. 7 is an explanatory view showing a positional relationship among terminal contact portions, an insulator contact portion and a pressing point in the gas sensor of the first embodiment.

The pressing point 332 at which the spring member 33 presses the proximal end insulator 31 is at such a position that it is projected within the triangle T shown in FIG. 7 formed by three straight lines connecting the insulator contact portion 316 and the terminal contact portions 322 of the pair. This makes it possible to reduce the contact pressure unevenness among the insulator contact portion 316 and the terminal contact portions 322 of the pair so that the sensor element 2 can be stably held by the terminal unit 3.

Figure 9:
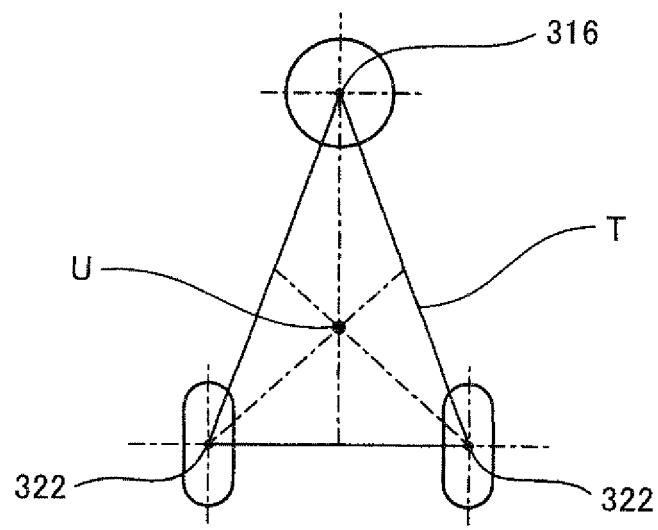
FIG. 9 is an explanatory view showing still another positional relationship among the terminal contact portions, insulator contact portion and pressing point in the gas sensor of the first embodiment.

When the pressing point 322 is at such a position that it is projected within the rectangle S shown in FIG. 8, the contact pressure unevenness among the insulator contact portion 316 and the terminal contact portions 322 of the pair can be further reduced so that the sensor element 2 can be further stably held by the terminal unit 3. When the pressing point 322 is at such a position that it is projected to the median point U shown in FIG. 9 of the triangle T, the sensor element 2 can be still more stably held by the terminal unit 3.

The metal terminal 31 includes the bent portion 324 located between the crimp-fixed portion 323 and the terminal contact portion 322. Accordingly, since an external force transmitted from the lead 17 is absorbed at the bent portion 324, the terminal contact portion 322 of the metal terminal 32 can be prevented from being affected by the external force.

The sensor element 2 projects toward the proximal end side of the gas sensor beyond the proximal end of the terminal unit 3. This makes it possible to prevent the metal terminals 32 opposite across from the sensor element 2 from being short-circuited to each other as explained as follows. It may occur that the metal terminals 32 are applied with an external force through the lead 17, and as a result they are deformed in a direction to approach each other at their portions closer to the proximal end side than the proximal end of the proximal end insulator 31 (especially, at their bent portions 324). In this case, if the sensor element 2 does not have a shape projecting toward the proximal end side beyond the proximal end of the terminal unit 3, since the deformation of the metal terminals 32 becomes large, they may be short-circuited to each other. Accordingly, in this embodiment, the sensor element 2 projects toward the proximal end side beyond the proximal end of the terminal unit 3, so that a short circuit between the metal terminals 32 can be prevented.

Figure 29:
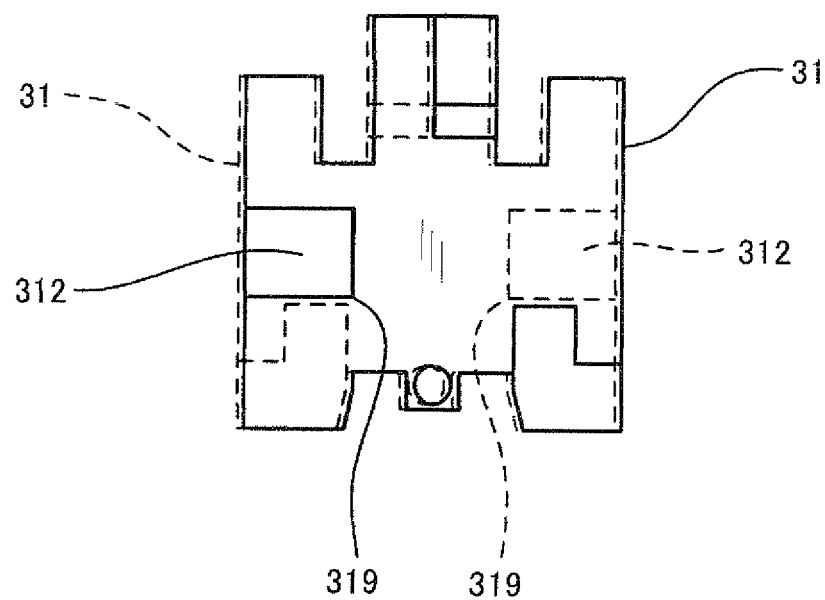
FIG. 29 is an explanatory view explaining a disadvantage when each of the proximal end insulators of the pair is formed with the single sensor positioning projection.

The proximal end insulator 31a, which is one of the pair of the proximal end insulators 31, includes the pair of the sensor positioning projections 312, while the other proximal end insulator 31b includes the pair of the insulator positioning projections 313. This facilitates to insert the sensor element 2 into the terminal unit 3 during assembly of the gas sensor 1. This is explained in more detail. In a case shown in FIG. 29 in which each of the proximal end insulators 31 includes one sensor positioning projection 312, if there is a positional deviation between the assembled proximal end insulators 31 (respectively shown by the solid line and broken line in FIG. 29), it may occur that the sensor element 2 is caught in a step portion 319 formed by the positional deviation between the sensor positioning projections 312. In this embodiment, since a pair of the sensor positioning projections are formed in one of the proximal end insulators 31, such a positional deviation can be prevented from occurring.

As has been explained above, according to this embodiment, there is provided a gas sensor exhibiting good and stable electrical conduction between the electrode pads and the metal terminals, and a method of manufacturing the gas sensor.

Second Embodiment

Figure 30A:
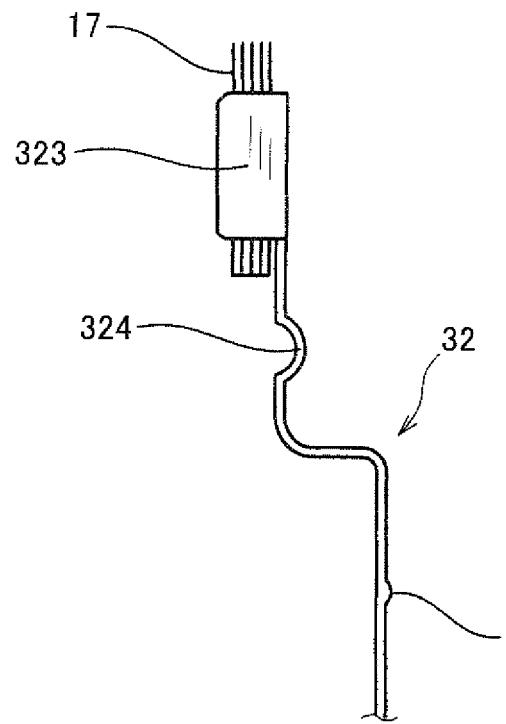
FIG. 30A is a side view of the metal terminal including a bent portion included in a gas sensor according to a second embodiment of the invention.
Figure 30B:
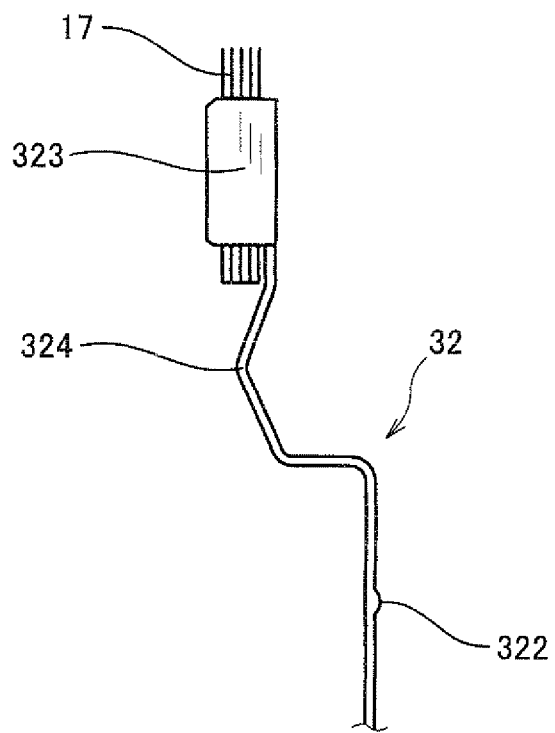
FIG. 30B is a side view of the metal terminal including a bent portion bent at an obtuse angle included in the gas sensor of the second embodiment.
Figure 31:
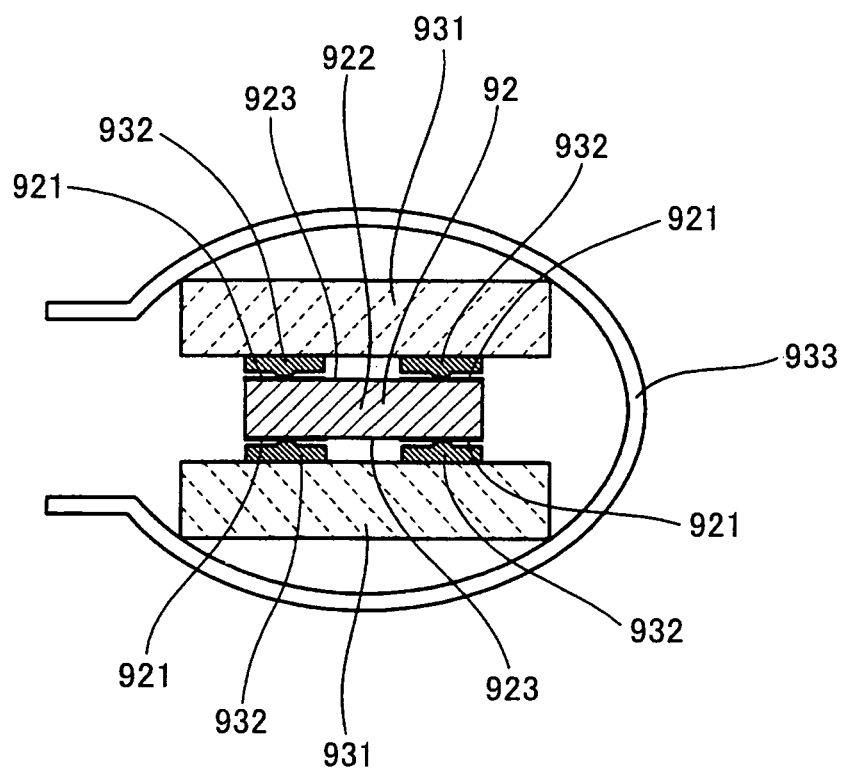
FIG. 31 is an explanatory cross-sectional view of proximal end insulators holding a sensor element included in a conventional gas sensor.

The second embodiment of the invention differs from the first embodiment in the shape of the bent portion 324 located between the crimp-fixed portion 323 and the terminal contact portion 322 of the metal terminal 32. The bent portion 324 may have any shape to prevent an external force applied to the crimp-fixed portion 323 from directly transmitting to the terminal contact portion 322. For example, the bent portion may have a shape shown in FIG. 30A in which its bent direction is opposite to that of the bent portion of the first embodiment, or a shape shown in FIG. 30B in which it is bent at an obtuse angle.

The gas sensor of the invention can be used, for example, as an A/F sensor (air-fuel ratio sensor) mounted on an exhaust pipe of an internal combustion engine to detect an air-fuel ratio by measuring oxygen concentration in an exhaust gas, or a NOx sensor to measure NOx concentration to thereby detect degradation of a ternary catalyst mounted on the exhaust pipe.

The above explained preferred embodiments are exemplary of the invention of the present application which is described solely by the claims appended below. It should be understood that modifications of the preferred embodiments may be made as would occur to one of skill in the art.

What is claimed is:

1. A gas sensor comprising:
a sensor element including a sensor cell and a heater, the sensor cell being made of an oxygen ion-conductive solid electrolyte body provided with sensor electrodes at both surfaces thereof, the heater including a heat generating section to generate heat for heating the sensor cell;
an insert-holding insulator insert-holding the sensor cell; and
a housing insert-holding the insert-holding insulator;
the sensor element including first and second pairs of electrode pads formed at portions thereof which are closer to a proximal end thereof in an longitudinal direction of the gas sensor than a portion thereof at which the sensor element is insert-held by the insert-holding insulator,
the electrode pads of the first pair being electrically connected to the heating section, the electrode pads of the second pair being connected to the sensor electrodes,
the electrode pads of the first pair being arranged side by side on a first electrode forming surface of the sensor element, the electrode pads of the second pair being arranged side by side on a second electrode forming surfaces of the sensor element, the first and second electrode forming surfaces being parallel to each other,
the gas sensor further comprising a terminal unit including a pair of proximal end insulators holding therebetween a proximal end portion of the sensor element at the first and second electrode forming surfaces, first and second pairs of metal terminals respectively provided in inner surfaces of the pair of the proximal end insulators, and a spring member pressing the pair of the proximal end insulators in a direction that the proximal end insulators approach each other,
each of the metal terminals of the first pair being connected to corresponding one of the electrodes pads of the first pair at a terminal contact portion thereof, each of the metal terminals of the second pair being connected to corresponding one of the electrodes pads of the second pair at a terminal contact portion thereof,
each of the proximal end insulators including an insulator contact portion in contact with a corresponding one of the first and second electrode forming surfaces,
the insulator contact portion of each of the pair of the proximal end insulators being located closer to the proximal end of the sensor element than the terminal contact portion of a corresponding one of the first and second pairs of the metal terminals, wherein
a pressing point at which the spring member presses one of the proximal end insulators is at such a position that the pressing point is projected within a triangle formed by connecting by three straight lines one of the insulator contact portions on the side of the pressing point and two of the terminal contact portions,
when a force is applied to a proximal end portion of one of the first and second pairs of the metal terminals in a direction to move the metal terminals away from the sensor element, the respective terminal contact point serves as a fulcrum and the respective insulator contact portions serve as a point of action, and
when a force is applied to said proximal end portion of one of the first and second pairs of the metal terminals in a direction to move the metal terminals toward the sensor element, the respective insulator contact portions serve as a fulcrum and the respective terminal contact portion serves as a point of action.

2. The gas sensor according to claim 1, wherein each of the insulator contact portions projects toward the corresponding sensor element from a surface of the corresponding proximal end insulator.

3. The gas sensor according to claim 1, wherein each of the proximal end insulators is formed with the single insulator contact portion.

4. The gas sensor according to claim 1, wherein each of the proximal end insulators is pressed at one pressing point by the spring member.

5. The gas sensor according to claim 1, wherein the spring member and each of the proximal end insulators are in contact with each other by concave and convex engagement.

6. The gas sensor according to claim 1, wherein a pressing point at which the spring member presses one of the proximal end insulators is at such a position that the pressing point is projected within a rectangle sharing the same median point with a triangle formed by connecting by three straight lines one of the insulator contact portion on the side of the pressing point and two of the terminal contact portions on the side of the pressing point, a width of the rectangle in a cross-longitudinal direction of the gas sensor being half a distance between the two of the terminal contact portions, and a longitudinal length of the rectangle is $2/3$ of a height of the triangle in the longitudinal direction.

7. The gas sensor according to claim 1, wherein a pressing point at which the spring member presses one of the proximal end insulators is at such a position that the pressing point is projected to a median point of a triangle formed by connecting by three straight lines one of the insulator contact portion on the side of the pressing point and two of the terminal contact portions on the side of the pressing point.

8. The gas sensor according to claim 1, wherein each of the metal terminals is electrically connected with a lead, and has a crimp-fixed portion crimp-fixed to one end of the lead and a bent portion located between the crimp-fixed portion and a corresponding one of the terminal contact portions.

9. The gas sensor according to claim 1, wherein the sensor element projects toward a proximal end side of the gas sensor beyond a proximal end of the terminal unit.

10. The gas sensor according to claim 1, wherein one of the proximal end insulators includes a pair of sensor positioning projections to position the sensor element in a cross-longitudinal direction of the gas sensor and parallel to the electrode forming surfaces, and the other of the proximal end insulators includes a pair of insulator positioning projections to position the other of the proximal end insulators with respect to the pair of sensor positioning projections.

* * * * *